(12) United States Patent
Isaacson et al.

(10) Patent No.: US 11,872,356 B2
(45) Date of Patent: Jan. 16, 2024

(54) ECHOGENIC CATHETER AND CATHETER SYSTEM

(71) Applicant: Becton, Dickinson and Company, Franklin Lakes, NJ (US)

(72) Inventors: S. Ray Isaacson, Layton, UT (US); Jeffrey C. O'Bryan, Murray, UT (US); Ralph L. Sonderegger, Farmington, UT (US); Marc Weimer, South Jordan, UT (US); Lawrence Trainer, Murray, UT (US); Seth R. Strand, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1069 days.

(21) Appl. No.: 16/238,090

(22) Filed: Jan. 2, 2019

(65) Prior Publication Data

US 2019/0209809 A1    Jul. 11, 2019

Related U.S. Application Data

(60) Provisional application No. 62/614,141, filed on Jan. 5, 2018.

(51) Int. Cl.
*A61M 25/01*    (2006.01)
*A61M 25/00*    (2006.01)
(Continued)

(52) U.S. Cl.
CPC ....... *A61M 25/0108* (2013.01); *A61B 8/0841* (2013.01); *A61L 29/18* (2013.01);
(Continued)

(58) Field of Classification Search
CPC ............ A61M 25/0108; A61M 25/005; A61M 25/0012; A61L 29/18
See application file for complete search history.

(56) References Cited

U.S. PATENT DOCUMENTS 4,027,659 A * 6/1977 Slingluff ........... A61M 25/0108
428/36.9
5,289,831 A * 3/1994 Bosley ................... A61B 90/39
128/899
(Continued)

FOREIGN PATENT DOCUMENTS

EP          2620111         7/2013
JP        2003190275 A      7/2003
(Continued)

*Primary Examiner* — James D Ponton
*Assistant Examiner* — Neeraja Gollamudi
(74) *Attorney, Agent, or Firm* — Kirton McConkie; Whitney Blair; Kevin Stinger

(57) ABSTRACT

A medical instrument or device, such as a catheter, has echogenic properties, in addition to or as an alternative to radiopaque properties, to facilitate detection of the medical instrument or device during medical procedures using suitable imaging methods, such as ultrasound imaging and/or x-ray imaging methods. In example embodiments, an example catheter has a relatively increased radiopacity and echogenicity to facilitate a clinician with detecting the catheter with ultrasound imaging and/or x-ray imaging methods to assist the clinician with the insertion, placement, and/or maintenance of the catheter, for example.

9 Claims, 2 Drawing Sheets

(51) Int. Cl.
*A61M 25/06* (2006.01)
*A61L 29/18* (2006.01)
*A61B 8/08* (2006.01)
*A61M 39/06* (2006.01)

(52) U.S. Cl.
CPC ...... *A61M 25/005* (2013.01); *A61M 25/0606* (2013.01); *A61M 25/0012* (2013.01); *A61M 2039/062* (2013.01)

(56) References Cited

U.S. PATENT DOCUMENTS

| | | | |
|---|---|---|---|
| 6,200,338 B1* | 3/2001 | Solomon | A61L 31/06 623/1.34 |
| 2003/0040756 A1* | 2/2003 | Field | A61M 5/00 606/108 |
| 2008/0154136 A1 | 6/2008 | Webler | |
| 2011/0172542 A1 | 7/2011 | Racz | |
| 2011/0213303 A1* | 9/2011 | Lentz | A61M 25/005 604/524 |
| 2012/0022502 A1* | 1/2012 | Adams | A61M 39/10 29/458 |
| 2012/0059308 A1* | 3/2012 | Hsu | A61M 19/00 604/528 |
| 2013/0204232 A1 | 8/2013 | Wieser et al. | |
| 2014/0025039 A1* | 1/2014 | Rajendran | A61B 17/3415 604/512 |
| 2015/0165160 A1 | 6/2015 | Thungana et al. | |
| 2016/0008517 A1 | 1/2016 | Burkholz et al. | |
| 2017/0112464 A1 | 4/2017 | Crisman et al. | |
| 2017/0325713 A1 | 11/2017 | Burkholz et al. | |
| 2017/0325714 A1 | 11/2017 | Sonderegger | |
| 2017/0347913 A1 | 12/2017 | Isaacson et al. | |
| 2017/0347914 A1 | 12/2017 | Isaacson et al. | |
| 2017/0348510 A1 | 12/2017 | Shevgoor et al. | |
| 2017/0348511 A1 | 12/2017 | Burkholz et al. | |

FOREIGN PATENT DOCUMENTS

| | | |
|---|---|---|
| JP | 2016513544 A | 5/2016 |
| WO | 98/19713 | 5/1998 |
| WO | 2017/210020 | 12/2017 |

* cited by examiner

ECHOGENIC CATHETER AND CATHETER SYSTEM

RELATED APPLICATIONS

This application claims the benefit of U.S. Provisional Patent Application No. 62/614,141, filed on Jan. 5, 2018, entitled "ECHOGENIC CATHETER AND CATHETER SYSTEM," which is incorporated herein in its entirety.

TECHNICAL FIELD

The present application relates generally to medical instruments or devices having echogenic properties or features, in addition to or as an alternative to, radiopaque properties or features, to facilitate detection of the medical instrument or device during medical procedures by suitable imaging methods, such as ultrasound imaging and/or X-ray imaging methods. More particularly, the present application relates to catheters having echogenic properties or features, in addition to or as an alternative to, radiopaque properties or features, to facilitate detection of the catheter by ultrasound imaging and/or X-ray imaging methods to assist a clinician with insertion, placement, and maintenance of the catheter during intravascular (IV) therapy, for example.

BACKGROUND

Peripheral IV catheter placement is the most common invasive hospital procedure and required by up to 90% of hospitalized patients. Clinical standards suggest removing IV catheters when clinically indicated; however, up to 50% of placed IV catheters are removed earlier than intended due to complications associated with the placement of the IV catheter.

Placing an IV catheter into a vein under the skin of a patient, particularly, a "difficult venous access" (DVA) patient, can be difficult. When a catheter is inserted into a vein of a DVA patient, ultrasound equipment is frequently used to help the clinician see the patient anatomy and then guide the IV catheter and needle into a proper position to facilitate IV therapy. However, the use of ultrasound imaging techniques requires a skilled clinician and an expensive ultrasound imaging device. Moreover, while ultrasound imaging may be useful to detect relatively dense materials, it may not detect less dense material, such as conventional catheters. The ability to detect the catheter using ultrasound imaging methods is particularly important after the needle is removed, e.g., to maintain the IV catheter properly placed during the IV therapy and/or retrieve dislodged, failed, or damaged catheters.

BRIEF SUMMARY OF SOME EXAMPLE EMBODIMENTS

In one aspect, a medical device includes a catheter adapter and a cannula extending distally from the catheter adapter. The cannula forms a lumen having a length between a first end and an opposing second end of the cannula. The lumen extends parallel to a longitudinal axis of the cannula and along at least a portion of the length. The cannula includes at least one echogenic stripe extending along at least a portion of the length of the cannula.

In another aspect, a catheter has a distal end and an opposing proximal end. The catheter includes a catheter adapter and a cannula extending distally from the catheter adapter. The cannula forms a lumen extending between the distal end and the proximal end of the catheter parallel to a longitudinal axis of the catheter. One or more stripes are formed in the cannula. The one or more stripes extend along at least a portion of a length of the cannula. The one or more stripes have echogenic properties or features.

In yet another aspect, a method for forming a stripe in a cannula of a catheter includes extruding a thermoplastic polymer material through an array of dies aligned such that a stripe made of a first thermoplastic polymer material and having echogenic properties or features is formed between and bonded to a second thermoplastic polymer material forming adjacent wall portions of a wall of the cannula.

BRIEF DESCRIPTION OF THE DRAWINGS

The detailed description is described with reference to non-limiting and non-exhaustive embodiments illustrated in the accompanying figures. The same reference numerals in different figures refer to similar or identical items.

DETAILED DESCRIPTION

Figure 1:
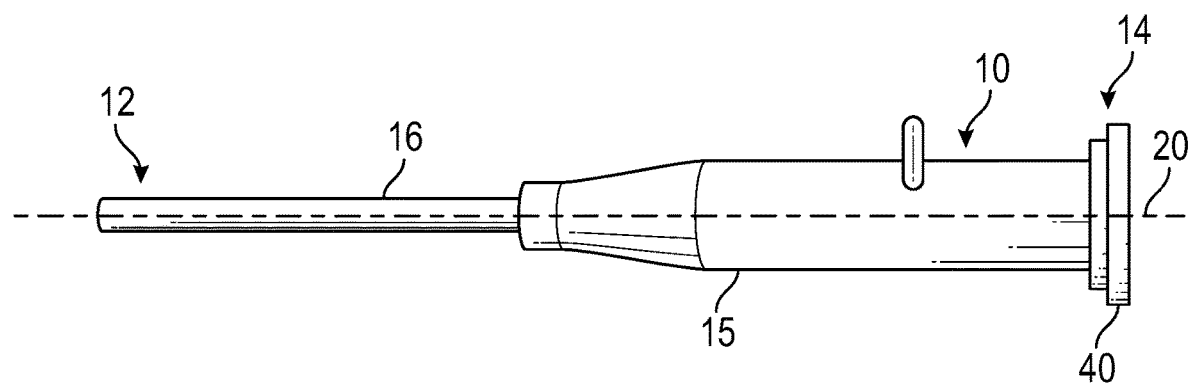
FIG. 1 is a perspective view of an example catheter, according to various embodiments.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

In example embodiments described herein, example medical instruments or devices, such as catheters, have echogenic properties or features, in addition to or as an alternative to, radiopaque properties or features, to facilitate detection of the medical instruments or devices during medical procedures using suitable imaging methods, such as ultrasound imaging and/or X-ray imaging methods. For example, in certain embodiments, example catheters have a relatively increased echogenicity to facilitate a clinician with detecting the catheter with ultrasound imaging methods to assist the clinician with the insertion and/or maintenance of the catheter, for example.

In example embodiments, an increased radiopacity or radio density increases the relative inability of certain electromagnetic radiation, e.g., a radio wave or an X-ray portion of the electromagnetic spectrum, to pass through a particular material. Radiopaque volumes of material have a white appearance on radiographs, compared with a relatively darker appearance of radiolucent volumes. For example, on typical radiographs, bones look white or light gray (radiopaque), whereas muscle and skin look black or dark gray, being mostly invisible (radiolucent). A radiopacifier contained in a medical devices enhances the visualization of the medical device during implantation for temporary implantation devices, such as catheters or guidewires, or for monitoring the position of permanently implanted medical devices, such as stents, hip and knee implants, and screws. While metal implants typically have sufficient radiocontrast such that an additional radiopacifier is not necessary, polymer-based devices may require incorporation of materials with high electron density contrast compared to the surrounding tissue. Examples of suitable radiocontrast materials include titanium oxide, tungsten, barium sulfate, zinc oxide, iron oxide, platinum oxide, and zirconium oxide.

Alternatively or in addition, an increased echogenicity increases an ability of the medical device to reflect an echo, e.g., return a signal during ultrasound examination. For example, when gas voids, cores, or bubbles are caught in an ultrasonic frequency field, the gas voids, cores, or bubbles may compress or oscillate to reflect a characteristic echo to generate a strong and unique sonogram in contrast-enhanced ultrasound. In certain embodiments, the gas voids, cores, or bubbles are composed of a suitable gas, such as air or heavy gases, e.g., perfluorocarbon or nitrogen.

When a catheter is inserted into a vein of a "Difficult Venous Access" (DVA) patient, ultrasound equipment is frequently used to help the clinician see the patient anatomy and then guide the IV catheter needle and catheter into the proper position to facilitate IV therapy. The use of ultrasound is useful but sometimes difficult to learn and master. For example, the plane of an ultrasound beam is very thin—several thousandths of an inch thick or wide and it is sometimes difficult for the clinician to see the catheter and associated needle when using ultrasound for placement of the catheter and needle.

Some conventional catheters or needles are echogenic (making the catheter or needle more visible by ultrasound imaging methods). In these conventional catheters or needles, material is added or a surface finish is changed or textured to better reflect the ultrasound energy. The increased texture reflects the ultrasound energy and appears on ultrasound images. However, an increase in material of the catheter or needle or texturing of a surface of the catheter or needle may undesirably promote thrombosis formation and/or blood clotting.

In example embodiments described herein, echogenic enhancing features are added to radiopaque stripes of the catheter tubing (e.g., gas bubbles, chemically formed bubbles, glass balloons, voids, irregularities, and/or relatively denser material such as tungsten, glass beads, or sand) while maintaining a smooth surface on the outer diameter (OD) and the inner diameter (ID) of the catheter tubing. In a particular embodiment, for example, virtually transparent tungsten particles having an average diameter less than 100 nanometers (nm) are added to radiopaque stripes to provide an increased radiopaque response and increased flashback visibility. Improving the echogenic features of the stripe can be accomplished in a variety of methods as described herein. For example, in certain example embodiments, chemical blowing agents are added into the radiopaque material of the stripes as the material is co-extruded with the traditional catheter material to provide these benefits while maintaining a very smooth finish on surfaces that may contact bodily fluids, such as blood. In alternative example embodiments, at least a portion of an outer surface of the cannula and/or at least a portion of an inner surface of the cannula forming the lumen includes an intentionally regularly patterned surface.

Figure 2:
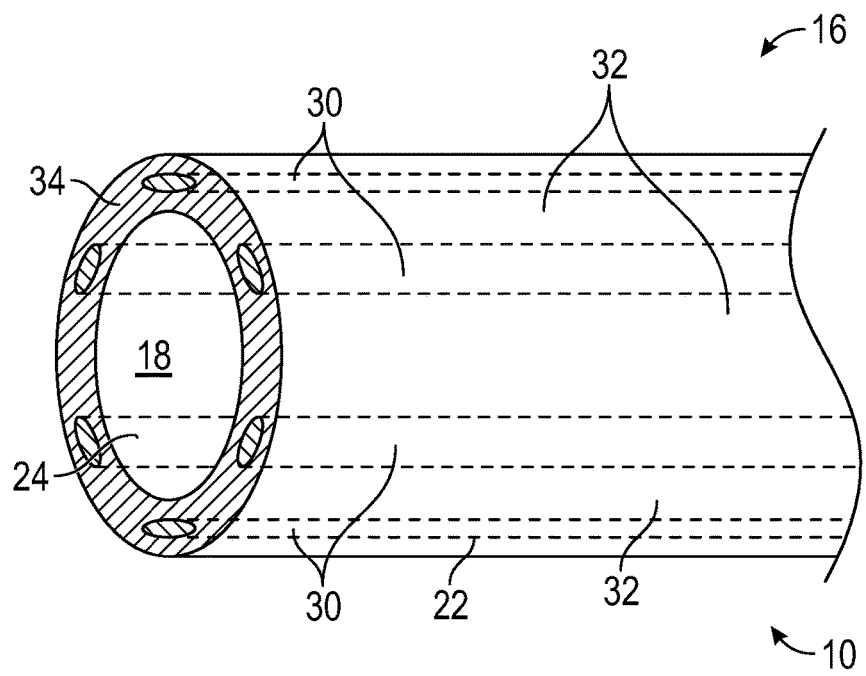
FIG. 2 is a portion of the example catheter shown in FIG. 1, according to various embodiments.
Figure 3:
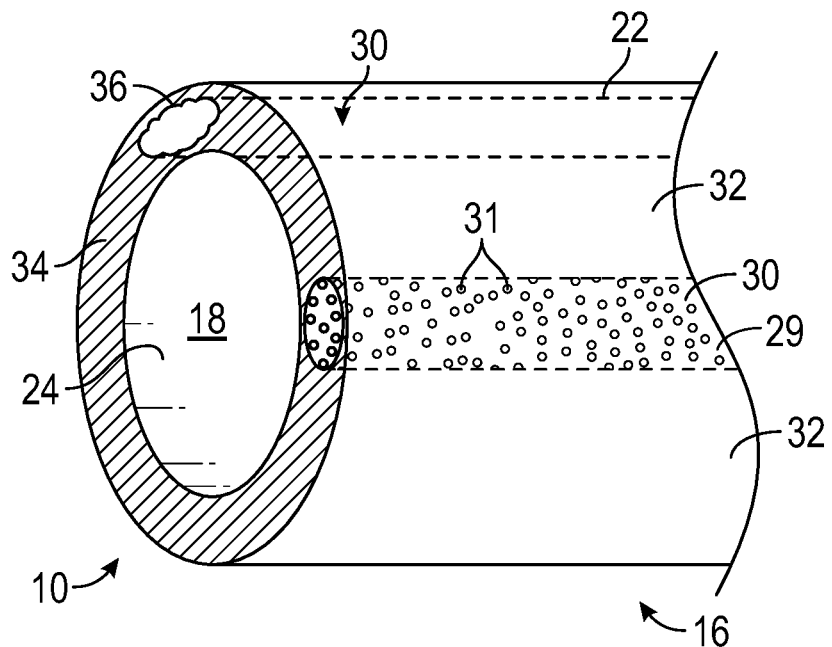
FIG. 3 is an enlarged section of the example catheter portion shown in FIG. 2, according to various embodiments.

Referring now to the figures, and initially to FIGS. 1-3, an example catheter 10 has a distal end 12 and an opposing proximal end 14. Catheter 10 includes a catheter adapter 15 and a cannula 16 extending distally from catheter adapter 15. In example embodiments, catheter adapter 15 is configured to couple catheter 10 to a small bore Luer taper lock fitting. Cannula 16 has a length extending from distal end 12 toward opposing proximal end 14 of catheter 10 in certain example embodiments. Catheter 10 forms or defines a lumen 18 extending between distal end 12 and proximal end 14 of catheter 10 along or parallel to a longitudinal axis 20 of catheter 10. In example embodiments, cannula 16 includes a thin tube having an outer diameter (OD) and an inner diameter (ID) forming lumen 18 that extends through catheter 10 and, in certain embodiments, beyond a distal end of catheter adapter 15 in the proximal direction. Referring further to FIGS. 2 and 3, in example embodiment, an outer surface 22 of cannula 16 (defining the outer diameter of cannula 16) and an opposing inner surface 24 of cannula 16 forming lumen 18 (defining the inner diameter of cannula 16) comprise a smooth, anti-thrombogenic surface to prevent or limit accumulation of tissue and/or fluids on the surface, e.g., coagulation or clotting of blood on outer surface 22 and inner surface 24.

In example embodiments, catheter adapter 15 is configured to couple to a cooperating small-bore fitting or connection, tubing, a hub, or another suitable connection such that lumen 18 provides a fluid flow path through catheter 10. In example embodiments, lumen 18 has a suitable diameter or a suitable cross-sectional dimension to facilitate fluid flow through catheter 10. Additionally or alternatively, lumen 18 may accommodate a medical device or instrument, such as a needle or an obturator, for example, which is movably positioned within lumen 18.

As shown in FIGS. 2 and 3, at least a portion of catheter 10, e.g., at least a portion of cannula 16 at distal end 12 of catheter 10, includes one or more stripes 30 having echogenic properties and/or features and/or radiopaque properties and/or features, e.g., a plurality of stripes 30 extending generally parallel to longitudinal axis 20 of catheter 10 along at least a portion of a length of catheter 10. In example embodiments, stripes 30 are formed in cannula 16 using a suitable method or technique to maintain the smooth outer surface 22 and inner surface 24 of cannula 16. For example, cannula 16 may be formed during a die extrusion process by extruding a suitable material, e.g., a biocompatible thermoplastic polymer material such as a polyurethane or fluoropolymer material, through an array of dies aligned such that each stripe 30 is formed between and bonded to extruded material forming adjacent transparent wall portions 32 of a wall 34 of cannula 16. In this extrusion process, a first thermoplastic polymer material is extruded through one or more secondary dies, e.g., a plurality of secondary dies, such as six secondary dies, to form respective stripes 30 having echogenic properties and/or features and/or radiopaque properties and/or features and a second thermoplastic polymer material is extruded through a major die to form transparent wall portions 32. As a result of this extrusion process, one or more stripes 30 are formed encapsulated into wall 34 of cannula 16 while maintaining the smooth outer surface 22 and smooth inner surface 24 of cannula 16. Because only stripes 30 include the echogenic properties and/or features and/or the radiopaque properties and/or features, the surface finish of cannula 16 is preserved. In alternative example embodiments, at least a portion of the outer surface of cannula 16 and/or at least a portion of the inner surface of cannula 16 forming lumen 18 includes an intentionally regularly patterned surface. Further, the clear or transparent wall portions 32 provide a clinician with visibility through cannula 16 to visualize blood flow through lumen 18, i.e., blood flow occurring in the annular space between the outer diameter of the needle inserted in lumen 18 and an inner diameter of cannula 16, to confirm proper placement of the needle tip in a patient's vein, for example.

As described above, in example embodiments, stripes 30 may include radiopaque properties or features. In example embodiments, stripes 30 include a biocompatible thermoplastic polymer material filled with a material or substance opaque to x-rays, thereby rendering stripes 30 visible under fluoroscopy or x-ray imaging. These fillers, or radiopacifiers, e.g., dense metal powders, affect the energy attenuation of photons in an x-ray beam as the x-ray beam passes through stripe 30, reducing an intensity of the photons by absorbing or deflecting them. Because stripes 30 exhibit a higher attenuation coefficient than soft tissue or bone, stripes 30 will appear lighter on a fluoroscope or x-ray film. This visibility may provide the contrast needed to accurately position or place catheter 10 in the desired vein. In particular embodiments, the image contrast and sharpness can be varied by a type and/or an amount of radiopacifier in stripes 30, and can be tailored to a specific application of catheter 10.

For example, a higher loading of radiopaque material may be needed for a thin-wall catheter cannula or tubing than for a catheter cannula or tubing with a thicker wall. The amount of additives may also be limited to prevent overloading, which may result in a loss of the material's mechanical properties. Suitable radiopacifiers for stripes 30 include, without limitation, barium sulfate, bismuth compounds (bismuth trioxide, bismuth subcarbonate, or bismuth oxychloride), tungsten, titanium, and zirconium oxide, which include metals that are excellent absorbers of x-rays. One or more radiopaque materials, e.g., a blend of barium sulfate and a bismuth compound, may be incorporated into stripes 30.

In addition to the radiopaque properties or features, or, in alternative embodiments, as an alternative, stripes 30 include echogenic properties or features. As shown, for example, in FIG. 3, in an example embodiment, stripes 30 include a plurality of voids 29 between outer surface 22 and inner surface 24 of cannula 16. In certain example embodiments, the plurality of voids 29 includes gas pockets or bubbles, e.g., air pockets or bubbles, formed in a thickness of each stripe 30 between outer surface 22 and inner surface 24 of cannula 16. Voids 29 may be formed in stripes 30 by infusing gas, e.g., air, into the thermoplastic polymer material used to form stripes 30 during the extrusion process such as described above. As gas is infused directly into the thermoplastic polymer material during the extrusion process, voids 29 are formed in stripes 30 to enhance the echogenicity of stripes 30.

Voids 29 may be formed in stripes 30 using other suitable methods. For example, in an example embodiment, a chemical foaming agent is added to the thermoplastic polymer material. In this embodiment, the chemical foaming agent decomposes during the extrusion process to form a gas that creates gas bubbles forming voids 29. Alternatively, various materials, such as ceramic beads or particles (e.g., glass or carbon beads or particles), metal beads or particles, and/or expandable thermoplastic blowing agents and/or lightweight fillers (e.g., Expancel microspheres), can be added to the thermoplastic polymer material to create voids 29. In certain embodiments, the void forming process may include a combination of these methods and/or other methods.

In an example alternative embodiment, also shown in FIG. 3, stripes 30 include one or more irregularities 36, e.g., a plurality of irregularities or discontinuities 36, formed in one or more stripes 30. The one or more irregularities or discontinuities 36 may include, without limitation, one or more bumps, grooves, valleys, peaks, ridges, and/or undulations, to enhance the echogenic reflective properties of the stripes. For example, a shape and/or a contour of stripes 30 may be changed from a general elliptical cross-section to a cross-sectional shape and/or a contour having, for example, bumps, grooves, valleys, peaks, ridges, undulations, and/or flower pedals, optimizing the echogenicity-enhancing properties of stripes 30 for ultrasound imaging methods. In certain embodiments, a change in the cross-sectional shape of stripes 30 and/or forming irregularities or discontinuities 36 or non-planar aspects in an outer surface of stripes 30 enhances the echogenic properties of stripes 30 potentially without having to add any additives to stripes 30. These changes to the cross-sectional shape of stripes 30 may be influenced by using a die having a corresponding profile or cross-sectional area rather than a conventional die having a circular or an elliptical cross-sectional area.

In alternative embodiments, stripes 30 may include a suitable, relatively dense material to create the echogenicity-enhancing properties of stripes 30. For example, stripes 30 may include a relatively dense material 31, such as sand, silica, fine particles, and/or glass beads. This dense material may also enhance the radiopacity of stripes 30. A combination of these methods to create the echogenicity-enhancing properties of stripes 30 may be used to offset a potential decrease in radiopacity resulting from the formation of voids 29 in stripes 30. Thus, the methods described herein can be utilized to form stripes 30 optimized to provide both echogenicity and radiopacity properties or features. In alternative example embodiments, at least a portion of catheter 10, e.g., at least a portion of cannula 16, includes one or more stripes 30 formed by or including a radiopaque and echogenic wire, e.g., a suitable metal wire.

The echogenic features can be staggered, stepped, or placed for better detection of catheter 10. For example, the echogenic properties of catheter 10 or a system including a needle, catheter 10, and/or a flashback notch, for example, can be segmented with echogenic features or properties and non-echogenic features or properties to provide additional information on needle tip, depth, and/or location, for example.

Referring again to FIG. 1, at proximal end 14, catheter 10 includes an adapter, such as a small-bore connector 40, for example. Small-bore connector 40 is configured to removably couple to any suitable medical device or component, for example, a cooperating small-bore fitting, a device, or a medical tubing. The medical device, component, or tubing may include a cooperating element, such as a cooperating small-bore connector, to facilitate coupling the medical device, component, or tubing, for example, to catheter 10. In the example embodiments, small-bore connector 40 includes a twist-lock mechanism to removably couple small-bore connector 40 to a cooperating small-bore connector having a cooperating twist-lock mechanism. Small-bore connector 40 can be easily disengaged from the cooperating small-bore connector by rotating small-bore connector 40 in an opposite direction with respect to the cooperating connector to disengage the threads. In alternative example embodiments, small-bore connector 40 may be a slip small-bore fitting that is pressed onto the cooperating small-bore connector.

Figure 4:
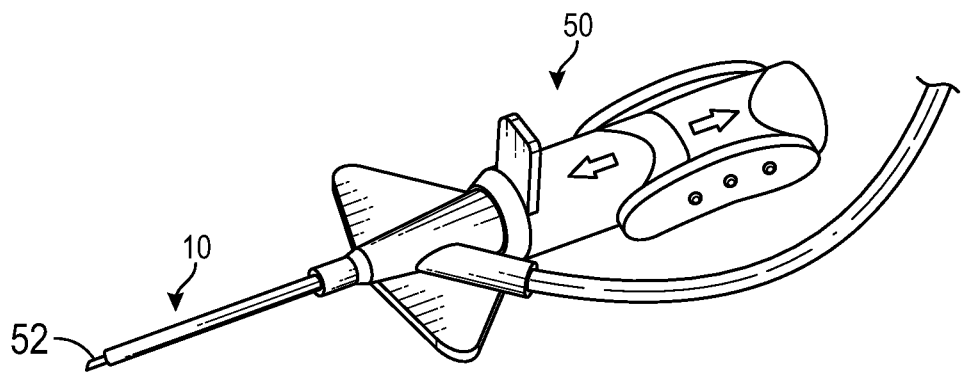
FIG. 4 is a perspective view of an example catheter system, according to various embodiments.

Referring to FIG. 4, in further example embodiments, the echogenic and, in some embodiments, radiopaque, catheter 10, as described herein, may be combined with other complimentary medical devices or instruments, such as a needle 52, to facilitate accessing veins in DVA patients, for example. Below are a few example combinations of devices, properties, and/or features that may provide for an example catheter system 50 including an example catheter 10 as described herein:

- a combination of the disclosed echogenic catheter and echogenic needle (or tip) technologies to provide an echogenic needle and an echogenic catheter, for example, as described in U.S. patent application Ser. No. 12/930,580, U.S. Patent Publication No. 2011/0172542, entitled "Ultrasound Guided Echogenic Catheter and Related Methods" and U.S. patent application Ser. No. 15/297,731, U.S. Patent Publication No. 2017/0112464, entitled "Echogenic Needle," each incorporated by reference herein in its entirety;
- a combination of the disclosed echogenic catheter and magnetic needle (and pre-magnetized) technologies, as shown in FIG. 4, for example, as described in U.S. patent application Ser. No. 15/154,353, U.S. Patent Publication No. 2017/0325713, entitled "Invasive Medical Device Cover with Magnet;" U.S. patent application Ser. No. 15/154,362, U.S. Patent Publication No. 2017/0325714, entitled "Electro-Magnetic Needle Catheter Insertion System;" U.S. patent application Ser. No. 15/170,518, U.S. Patent Publication No. 2017/0348510, entitled "Medical Devices, Systems and Methods Utilizing Permanent Magnet and Magnetizable Feature;" U.S. patent application Ser. No. 15/170,497, U.S. Patent Publication No. 2017/0347913, entitled "Invasive Medical Devices Including Magnetic Region and Systems and Methods;" U.S. patent application Ser. No. 15/170,531, U.S. Patent Publication No. 2017/0347914, entitled "Invasive Medical Devices Including Magnetic Region and Systems and Methods;" and U.S. Patent Application No. 62/481,964, entitled "A System for Insertion Visualization of a Vascular Access Device with Multiple Magnetic Features on a Needle Assembly," each incorporated by reference herein in its entirety;
- a combination of the disclosed echogenic catheter with guidewire placement technologies to provide an echogenic needle tip, magnetic needle tip and an echogenic catheter in a device or a system, for example, as described in U.S. patent application Ser. No. 15/604,244, U.S. Patent Publication No. 2017/0348511, entitled "Medical Devices, Systems and Methods Utilizing Permanent Magnet and Magnetizable Feature," incorporated by reference herein in its entirety;
- a combination of the disclosed echogenic catheter with a reduced bevel length or shortened needle geometry for better first stick success, for example, as described in U.S. Patent Application No. 62/541,205 filed on Aug. 4, 2017, entitled "Introducer Needle for Catheter Placement," incorporated by reference herein in its entirety; and/or
- a combination of the disclosed echogenic and radiogenic catheter with anti-infective coatings, such as an antimicrobial, silver coating, or copper coating, for example, as described in U.S. patent application Ser. No. 14/326,036, U.S. Patent Publication No. 2016/0008517, entitled "Antimicrobial Coating and Kink Resistant Feature for Vascular Access Devices," incorporated by reference herein in its entirety.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims. One skilled in the art will realize that a virtually unlimited number of variations to the above descriptions are possible, and that the examples and the accompanying figures are merely to illustrate one or more examples of implementations. It will be understood by those skilled in the art that various other modifications can be made, and equivalents can be substituted, without departing from claimed subject matter. Additionally, many modifications can be made to adapt a particular situation to the teachings of claimed subject matter without departing from the central concept described herein. Therefore, it is intended that claimed subject matter not be limited to the particular embodiments disclosed, but that such claimed subject matter can also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter can be practiced without these specific details. In other instances, methods, devices, or systems that would be known by one of ordinary skill have not been described in detail so as not to obscure claimed subject matter.

Reference throughout this specification to "one embodiment" or "an embodiment" can mean that a particular feature, structure, or characteristic described in connection with a particular embodiment can be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described can be combined in various ways in one or more embodiments. In general, of course, these and other issues can vary with the particular context of usage. Therefore, the particular context of the description or the usage of these terms can provide helpful guidance regarding inferences to be drawn for that context.

Various implementations have been specifically described. However, many other implementations are also possible.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

What is claimed is:

1. A medical device, comprising:
a catheter adapter; and
a cannula forming a lumen having a length between a first end and an opposing second end of the cannula, the lumen extending parallel to a longitudinal axis of the cannula and extending along at least a portion of the length, the cannula comprising a wall and a plurality of stripes encapsulated into the wall and extending along at least a portion of the length of the cannula, wherein the plurality of stripes are constructed of a first thermoplastic polymer material filled with both a plurality of radiopacifiers and a plurality of echogenic voids, wherein the wall is constructed of a second thermoplastic polymer material and forms an outer surface of the cannula and an inner surface of the cannula proximate the lumen, wherein the first thermoplastic polymer material is bonded to the second thermoplastic polymer material, wherein each of the plurality of stripes is encapsulated by the second thermoplastic polymer material, wherein the plurality of echogenic voids form an irregular outer surface of each of the plurality of stripes, wherein the plurality of echogenic voids are spaced apart from the outer surface of the cannula and the inner surface of the cannula such that outer surface of the cannula and the inner surface of the cannula are smooth having a shape not affected by the plurality of echogenic voids.

2. The medical device of claim 1, wherein each of the plurality of stripes comprises a plurality of glass beads or sand formed therein.

3. The medical device of claim 1, wherein at least one of the outer surface of the cannula and the inner surface of the cannula forming the lumen includes an intentionally regularly patterned surface.

4. The medical device of claim 1, wherein the second thermoplastic polymer material forms a plurality of transparent wall portions that equally space apart the plurality of stripes.

5. A method for forming a stripe of the plurality of stripes in the cannula of the medical device of claim 1, the method comprising extruding the first thermoplastic polymer material and the second thermoplastic polymer material through an array of dies aligned such that the stripe is formed of the first thermoplastic polymer material and is formed between and bonded to the second thermoplastic polymer material forming adjacent wall portions of the wall of the cannula.

6. The method of claim 5, further comprising infusing gas into the first thermoplastic polymer material to form the plurality of echogenic voids in the stripe.

7. The method of claim 5, further comprising adding a chemical foaming agent to the first thermoplastic polymer material to form the plurality of echogenic voids in the stripe.

8. The method of claim 5, further comprising adding ceramic beads or particles, metal beads or particles, and/or expandable thermoplastic blowing agents and/or lightweight fillers to the first thermoplastic polymer material to form the plurality of echogenic voids in the stripe.

9. The method of claim 5, wherein the stripe has radiopaque properties or features.

* * * * *